(12) United States Patent
Schwarz et al.

(10) Patent No.: US 7,978,810 B2
(45) Date of Patent: Jul. 12, 2011

(54) IMAGING METHOD FOR VARIABLE PITCH SPIRAL CT AND A CT MACHINE FOR CARRYING OUT THE METHOD

(75) Inventors: Karl Schwarz, Roth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 271 days.

(21) Appl. No.: 12/149,487

(22) Filed: May 2, 2008

(65) Prior Publication Data

US 2008/0285709 A1    Nov. 20, 2008

(30) Foreign Application Priority Data

May 4, 2007   (DE) .......................... 10 2007 021 023

(51) Int. Cl.
*A61B 6/00*    (2006.01)
(52) U.S. Cl. .............................................. 378/4; 378/19
(58) Field of Classification Search ................. 378/4, 19
See application file for complete search history.

(56) References Cited

U.S. PATENT DOCUMENTS

| | | | | |
|---|---|---|---|---|
| 6,108,575 | A * | 8/2000 | Besson .......................... | 600/425 |
| 7,583,777 | B2 * | 9/2009 | Tang et al. ........................ | 378/4 |
| 7,724,866 | B2 * | 5/2010 | Naidu et al. ..................... | 378/15 |
| 2003/0133533 | A1 * | 7/2003 | Bruder et al. ..................... | 378/4 |
| 2005/0074085 | A1 * | 4/2005 | Hsieh et al. ....................... | 378/4 |
| 2006/0029180 | A1 * | 2/2006 | Katsevich ......................... | 378/4 |
| 2006/0050842 | A1 * | 3/2006 | Wang et al. ...................... | 378/16 |
| 2007/0053480 | A1 * | 3/2007 | Nishide et al. .................... | 378/4 |
| 2007/0110211 | A1 * | 5/2007 | Hsieh et al. ..................... | 378/16 |

FOREIGN PATENT DOCUMENTS

| DE | 102005038561 | 2/2006 |
|---|---|---|
| WO | WO 2004/084137 | 9/2004 |

OTHER PUBLICATIONS

Stierstorfer et al., Weighted FBP—a simple approximate 3D FBP algorithm for multislice spiral CT with good dose usage for arbitrary pitch, Phys Med Biol, 49, 2004, pp. 2209-2218.*

* cited by examiner

*Primary Examiner* — Edward J Glick
*Assistant Examiner* — Alexander H Taningco
(74) *Attorney, Agent, or Firm* — Harness, Dickey & Pierce, P.L.C.

(57) ABSTRACT

An imaging method is disclosed for variable pitch spiral CT. In at least one embodiment, the method includes spiral scanning of an examination object lying on a patient table, with the aid of a beam emanating from at least one focus, and the aid of a detector arrangement of planar design lying opposite the focus, the detector arrangement supplying output data that represent the attenuation of the beams during passage through the examination object; filtering the output data; weighted back projection of the filtered output data; and visualizing a layer or a volume on a display unit on the basis of the back projected output data. In at least one embodiment, a non constant pitch of the spiral scanning is taken into account computationally during the back projection. In at least one embodiment, a CT machine is disclosed for carrying out the above named method.

13 Claims, 5 Drawing Sheets

Geringer (langsamer) Pitch

Hoher (schneller) Pitch

IMAGING METHOD FOR VARIABLE PITCH SPIRAL CT AND A CT MACHINE FOR CARRYING OUT THE METHOD

PRIORITY STATEMENT

The present application hereby claims priority under 35 U.S.C. §119 on German patent application number DE 10 2007 021 023.1 filed May 4, 2007, the entire contents of which is hereby incorporated herein by reference.

FIELD

Embodiments of the present invention relate in general to an image reconstruction method, based on back projection, in computed tomography. At least one embodiment of the present invention generally relates, in particular, to a method for imaging in computed tomography in the case of which in accordance with a spiral data acquisition the examination object is moved at a different (and thus variable) speed relative to the x-ray detector unit (gantry) that is to say the CT system has a variable pitch during spiral scanning. At least one embodiment of the invention further generally relates to a CT machine that is suitable for carrying out this method.

BACKGROUND

A very popular method, for example, what has come to be known in English as "Filtered Back Projection (FBP)". In this type of CT imaging, the examination object is penetrated—starting from an x-ray source (x-ray tube, focus)—by a, for example, conical or pyramidal beam that is captured, more or less attenuated after penetration by a detector array of planar design. The measured values are filtered in a suitable way and back projected, as a result of which at least one slice image is obtained that, owing to the different absorption values of the respective x-rays, represents the anatomy in this slice region by different grey scale values.

The so-called "weighted FBP method" has been developed in order to avoid "cone beam artifacts" produced because of the conical or pyramidal x-ray beam, and to make better use in the interest of an optimized beam dose of redundant data such as are produced during spiral scans with a low table feed owing to multiple irradiation of one and the same voxel and also to avoid redundancy artifacts.

The spiral scanning just mentioned constitutes an alternative to conventional or sequential CT imaging that cannot be wished away. The development of slip ring technology has rendered it possible for the scanning system, that is to say the tube detector array arrangement, to be continuously rotated. If the patient table is likewise subjected to continuous feed during this rotation, the x-ray source revolves around the patient on a spiral or a helix. The object to be examined can be recorded over a large volume in this way without any gaps, recording time for such a large volume being decisively shortened by comparison with conventional tomography. Recording without any gaps means: all the points along the z-axis (spiral axis) have been trans-radiated at least once. At least partial information is present for the reconstruction from each layer, which can subsequently be selected at will. Missing data of this layer can be supplemented by interpolation (if necessary, after appropriate rebinning), after which all known two- or three-dimensional reconstruction methods are available again without restriction.

DE 102005038561 A1 discloses a variable pitch with the aim of optimally recording the contrast medium by way of an x-ray CT machine.

Again, WO 2004084137 A2 discloses a variable pitch with a novel reconstruction algorithm based on interpolation.

SUMMARY

The inventors have realized that there is a great interest in medical imaging, in particular in computed tomography, in being able to vary at will the table feed or the pitch during a spiral CT examination—for example to raise it in sections—in order to record subregions of the examination object that are of less interest only coarsely, that is to say as an overview, or, for example, to diminish it along another section in order to visualize an important subsection of the examination object (for example one or more organs to be diagnosed) with a high resolution without, however, having to interrupt the process of data acquisition.

In at least one embodiment of the invention, a method is specified that enables a faster, more effective artifact-free image reconstruction in spiral CT imaging even given a variable pitch during data acquisition.

In at least one embodiment of the present invention by the features of the independent claim. The dependent claims develop the central idea of the invention in a particularly advantageous way.

Consequently, according to at least one embodiment of the invention an imaging method for variable pitch spiral CT, includes:

S1: spiral scanning of an examination object lying on a patient table, with the aid of a beam emanating from at least one focus, and the aid of a detector arrangement of planar design lying opposite the focus, the detector arrangement supplying output data that represent the attenuation of the beams during passage through the examination object, S2: filtering the output data, S3: weighted back projection of the filtered output data, S4: visualizing a layer or a volume on a display unit on the basis of the back projected output data, a non constant pitch of the spiral scanning being taken into account computationally during the back projection, and the non constant pitch being described in the form of a function f that describes the location of the patient table as a function of the focus angle $\alpha$, and f being expressed by a mathematical relationship between the projection angle $\theta$, the column coordinate p of the detector arrangement and $R_F$ as radius of the spiral, characterized in that the mathematical relationship is approximated via approximations, a first approximation taking account of the actual position of a parallel projection and of the current pitch of the spiral and basing a local linearization of the spiral profile thereon, or a second approximation taking account of the actual position of a parallel projection and of the current pitch of the spiral and basing an approximation of the spiral profile in the form of an average pitch thereon, or a third approximation being implemented by an approximation of the position of a parallel projection as well as of the current pitch of the spiral by means of an average pitch and an effective initial position of the focus angle.

In one possible embodiment of the inventive method, the f expressed by $\theta$, p and $R_F$ in the case of the back projection features in the calculation of the row coordinate q.

The focal path that is a spiral relative to the patient advantageously comes about owing to the fact that the focus is moved on a circular path about the system axis, and a relative movement between the focus and the examination object is performed simultaneously in the direction of the system axis.

Furthermore, it is advantageous to form the detector arrangement from detector elements arranged in matrix form in columns and rows.

Furthermore, there is claimed according to at least one embodiment of the invention a CT machine is suitable for carrying out a method of at least one embodiment.

Likewise, at least one embodiment relates to a computer software product which implements at least one embodiment of the method in the form of programs or program modules when it runs on a computing device connected to a CT machine.

Further advantages, features and properties of the present invention are explained in more detail below with the aid of example embodiments and with reference to the accompanying drawings, in which:

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
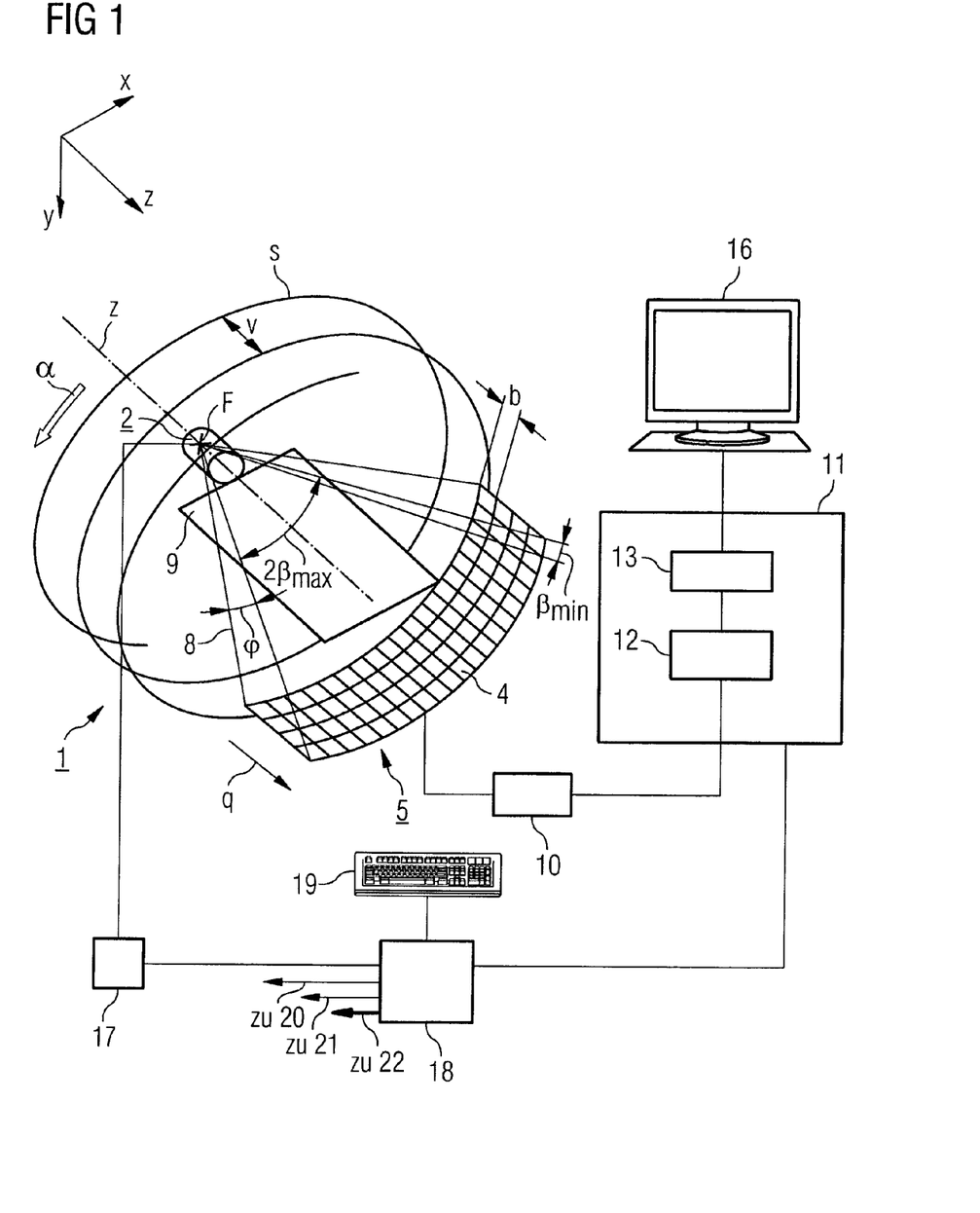
FIG. 1 shows a schematic, partly in perspective and partly as a block diagram, of a CT machine whose detector has a number of rows of detector elements.
Figure 2:
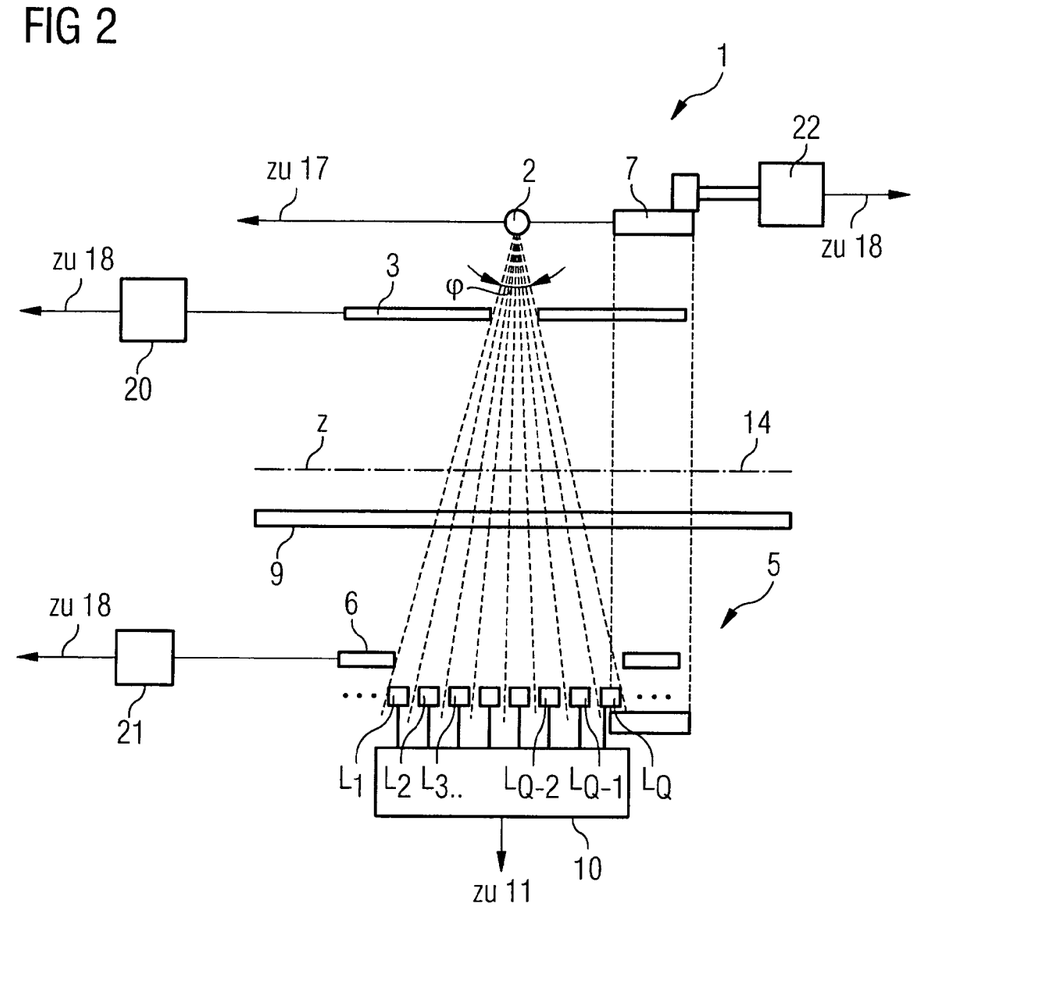
FIG. 2 shows a longitudinal section through the CT machine of FIG. 1.

FIGS. 1 and 2 illustrate a third generation CT machine that is suitable for carrying out an embodiment of the inventive method. Here, FIGS. 1 and 2 illustrate the same operating mode. The measuring arrangement 1 has an x-ray source 2 in front of which a near source beam collimator 3 is arranged (FIG. 2). The multi-row detector 5 is a surface array of a number of a number of rows and columns of detector elements 4. The rows have the width b, the columns the width $\beta_{min}$. The position of a detector element 4 in the row direction is uniquely fixed by the fan angle $\beta$ in the case of the fan beam geometry. The position of the detector element in the column direction (z-direction) is uniquely defined by the column index q. Furthermore a near detector beam collimator 6 is arranged in front of the detector system 5 (FIG. 2). For the sake of clarity only eight rows of the detector elements 4 are illustrated in FIGS. 1 and 2 ($L_Q$; Q=1 to 8). However, the detector system 5 has further rows of detector elements 4 (up to 32 rows and more in modern machines), which can be used for measurement dependent on the aperture of the collimator 6 (indicated by black dots in FIG. 2).

The x-ray source 2 with the beam collimator 3, on the one hand, and the detector system 5 with the beam collimator 6, on the other hand, are fitted opposite one another on a rotary frame 7. During operation of the CT machine, the adjustable rectangular or round beam collimator 3 lends the beam emanating from the x-ray source 2 in pyramidal or conical shape such that all the rays of the beam—that is to say also the marginal rays 8—impinge exactly on the detector system 5 owing to the beam collimator 6 of the same geometry (but with a greater aperture).

For reasons of dose efficiency and patient protection (compliance with the specific absorption rate, SAR), it is necessary for the two beam collimators 6 and 3 to be tuned to one another. The collimator 3 influences the level of the radiation input into the object to be examined, and thus the SAR. The collimator 6 exposes only that region of the detector system 5 which can be directly struck by the x-ray beam. In the operating mode illustrated in FIGS. 1 and 2, this is eight rows of detector elements 4, which are denoted below as active rows. The further rows (indicated by black dots) are covered by the beam collimator 6, and are therefore not active. If the aperture of the collimator 3 is set to be too large, or the opening of the collimator 6 to be too small, the patient is unnecessarily contaminated by marginal rays that cannot contribute to imaging.

As already mentioned, each row of detector elements 4 has a number K of detector elements, the indexed fan angle $\beta_k = \beta_1$ to $\beta_K$ constituting the channel index, and each detector element being assigned such a fan angle $\beta_k$. The fan angle of the middle detector element is, however, equal to zero by definition; the fan angles of the two outermost detector elements are $\beta_1 = +\beta_{max}$ and $\beta_K = -\beta_{max}$.

The active rows of detector elements 4, which are denoted by $L_q$, have likewise already been mentioned, q constituting the row index and covering a range from 1 to Q. $L_1$ to $L_Q$ therefore represent all the detector elements participating in the measurement process, which in the case of the exemplary embodiment described correspond approximately in each case to the z-coordinates of the image pixels or image voxels.

The x-ray beam further has the cone angle $\phi$ plotted in FIGS. 1 and 2, which is the aperture angle of the x-ray beam in a plane containing the system axis Z and the focus F. The other aperture angle of the x-ray beam (fan aperture angle) constitutes the double angle $2\beta_{max}$ already mentioned, which is measured at right angles to the system axis Z and defines a plane that includes the focus F of the x-ray source. $2\beta_{max}$ is depicted in FIG. 1 by way of illustration.

The rotary frame 7 can be set rotating about the system axis Z by way of a drive device 22. The system axis Z runs parallel to the z-axis of a three-dimensional rectangular coordinate system illustrated top left in FIG. 1.

The columns of the detector system 5 also likewise run in the direction of the z-axis, while the rows, whose width b is measured in the direction of z-axis and is, for example, 1 mm, run transverse to the system axis Z or the z-axis.

In order to be able to introduce an examination object, for example a patient, into the beam path of the x-ray beam, a bearing apparatus 9 is provided that can be displaced parallel to the system axis Z (that is to say, in the direction of the z-axis) specifically in such a way that the rotation movement of the rotary frame 7 and the translation movement of the bearing apparatus can be tuned to one another, that is to say the ratio of translation speed to rotation speed can be set as desired for the purpose of the present invention. According to the invention, it is to be possible to be able to select for a specific region of the z-axis a desired faster, or else slower value for the feed d of the bearing apparatus per revolution of the rotary frame, and thus to be able to keep the pitch within sensible limits, but to keep it variable in any case. The pitch is defined in general as the ratio of table feed d to layer collimation Q·b $$p = \frac{d}{Q \cdot b} \tag{1}$$

It is possible in this way for different regions of the volume of an examination object located on the bearing apparatus 9 to be scanned at different speeds in the course of a whole body volume scan, depending on the priority of the corresponding body region stipulated by the user (generally the doctor). According to an embodiment of the invention, such a speed of the focus relative to the patient is described mathematically as a function f of the focus angle $\alpha$. A discontinuous volume scan in the form of an inhomogeneous spiral scan can either be undertaken by varying the translation of the bearing apparatus 9 in a corresponding z-section while the rotation of the measuring unit 1 is unchanged, or by varying the rotational speed of the focus F of the x-ray source relative to the bearing apparatus 9, or else undertaking both variations simultaneously, such that a spiral path denoted in FIG. 1 by S has a variable pitch in sections:

Low pitch: spiral revolutions lie very close to one another, that is to say recording a multiplicity of projections from various projection directions; high energy input, but also high resolution.

High pitch: large spacing of the adjacent spiral revolutions, that is to say recording fewer projections from different projection directions; lower energy input associated with a low resolution.

The mathematics of FBP image reconstruction indicates that when recording data using fan beam geometry the spiral scanning in the $\beta$-direction must extend at least over an angle range of $\pi + 2\beta_{max}$, in order to allow the complete reconstruction of one CT image per row of detector elements (however, it can also be arbitrarily longer within the technical limits of the CT machine). When data has been recorded using parallel beam geometry, data acquisition over an angle range of only 180° suffices in principle. That is to say, $P_{x,y,z}(\theta+180°,p,q)$ is also known with each measured projection data record $P_{x,y,z}(\theta, p, q)$ in parallel beam geometry. Consequently, a second spiral (an additional helix) is obtained that is displaced by an angular offset of 180° in comparison with the basic spiral. The reason for this is the physical property of the x-rays that their attenuation along the beam path is invariant as regards reversal of direction.

The measured data that are read out in parallel during spiral scanning from detector elements of each active row of the detector system 5 and correspond to the individual projections $P(\alpha,\beta,q)$ in fan beam geometry, are subjected to digital/analogue conversion in a data conditioning unit 10, serialized and transmitted to an image computer 11.

After measured data have been preprocessed in a preprocessing unit 12 of the image computer 11, the resulting data stream passes to a slice image reconstruction unit 13 that reconstructs from the measured data slice images of desired layers of the examination object by using an inventive method, still to be described in detail, based on "weighted filtered back projection", WFBP.

In general, the CT images are composed of pixels (pixel=picture element, arranged in a matrix-like manner, the pixels being assigned to a respective image plane. Furthermore, each pixel is assigned a CT number in Hounsfield units (HU), the individual pixels being displayed in a gray scale value corresponding to their respective CT number in accordance with a CT number/gray scale. Here, each pixel illustrates a volume element or a voxel (voxel=volume element) in the corresponding layer of the examination object.

As a consequence of the multi-row nature of the detector system 5 and of the spiral scanning, measured data are obtained with reference to a number of layers of the examination object. These are available as 3D data and must be subjected to 3D back projection because of the WFBP. The end result supplies 3D image data in the form of a three-dimensional matrix (for example in an x-, y-, z-coordinate system) each element of the matrix corresponding to a voxel (for example V(x,y,z)) and including the gray scale value corresponding to the associated CT number. Those elements of the three-dimensional matrix that have in their totality the same x-, y-, or z-value then respectively constitute a planar slice image of the corresponding x-, y-, or z-layer of the examination object.

The images reconstructed by the slice image reconstruction unit 13 are displayed on the display unit 16 for example a monitor, connected to the image computer 11.

The x-ray source 2 (for example an x-ray tube) is supplied by a generator unit 17 with the required voltages and currents for example the tube voltage U. In order to be able to set these to the respective required values, the generator unit 17 is assigned a control unit 18 with a keyboard 19 that permits the required settings.

The remaining operation and control of the CT machine are also performed by way of the control unit 18 and the keyboard 19, this being symbolized by the pictorial connection of the control unit 18 to the image computer 11.

As stated, the position of the beam connectors 3 and 6, and thus the number Q of the active rows of detector elements 4, can be set, for which purpose the control unit 18 is connected to adjusting units 20 assigned to the beam connectors 3 and 6. It is also possible to set the rotation time τ that is required by the rotary frame 7 for a complete revolution, this being illustrated by the connection between the drive unit 22 assigned to the rotary frame 7 and the control unit 18.

Although it is possible in principle to implement at least one embodiment of the inventive imaging method for variable pitch spiral CT by using fan beam geometry as well, embodiments of the invention are explained without restriction of generality by using parallel beam geometry, since the latter is simpler and requires far less computing time.

However, for reasons of technical advantages the data acquisition of a spiral CT is generally carried out using fan beam geometry. Thus, the object initially is to convert the measurement result obtained using fan beam geometry (the 3D data record obtained) to parallel beam geometry. There is a multiplicity of algorithms for this purpose that are all based on a so-called rebinning of the measurement points.

The rebinning of the data, obtained using fan beam geometry, to parallel beam geometry is performed in such a way that rays that are parallel to one another and can therefore be combined in a suitable way to form a projection in parallel beam geometry are extracted from different projections acquired using fan beam geometry. The reason for this complicated procedure consists in the pyramidal or conical character of the beam in which no single pair of parallel rays exists.

As already mentioned, in parallel beam geometry data from an angle interval of length $\pi=180°$ suffice to reconstruct a complete image for the purpose of image reconstruction in parallel geometry. Since, however, the data must for the most part be obtained using fan beam geometry, it is necessary for data from an interval of length $180°+2\beta_{max}$ to be available.

Figure 3:
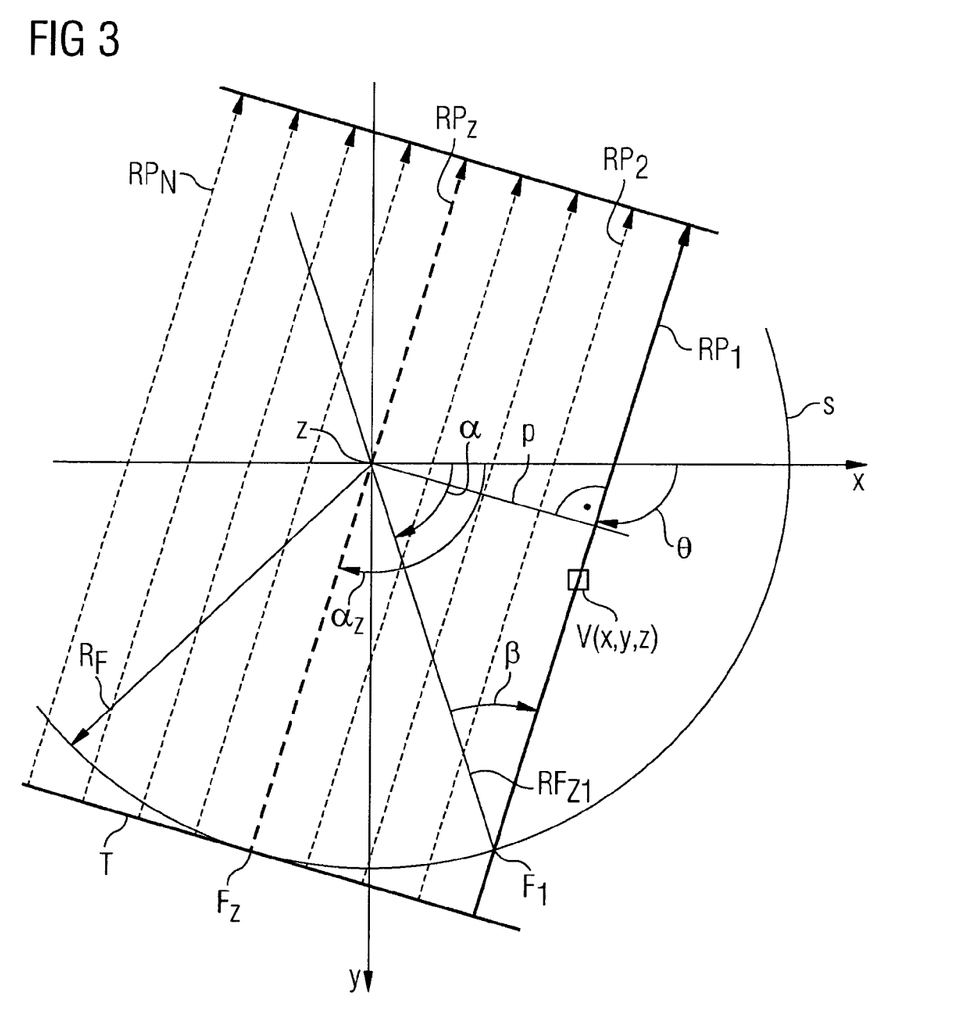
FIG. 3 shows a schematic of a parallel beam geometry derived from the fan beam geometry by rebinning and based on the WFBP method.

FIG. 3 illustrates a projection in parallel beam geometry. All n parallel rays $RP_1$ to $RP_N$ of this projection assume the parallel fan angle θ to the x-axis of the coordinate system illustrated in FIG. 3 and corresponding to that in accordance with FIG. 1.

The transition from fan beam to parallel beam geometry is to be explained below with the aid of the parallel ray $RP_1$ (solid arrow printed in bold on the right hand side) illustrated in FIG. 3.

The parallel ray $RP_1$ originates from a projection, obtained using fan beam geometry, that was acquired in the case of the focal position $F_1$ on the focal path S. The central beam $RF_{Z1}$ belonging to this projection in fan beam geometry (central ray because this runs through the axis of rotation 14 and thus through the z-axis of the coordinate system) is likewise illustrated in FIG. 3. The focal position $F_1$ corresponds to the focus angle $\alpha_1$; this is the angle that the x-axis and the central ray $RF_{Z1}$ enclose with one another. The central ray $RF_{Z1}$ encloses with the (marginal) ray $RP_1$ the angle β, which is also termed fan angle. It is easy to see that it holds for the parallel fan angle θ that:

$$\theta = \alpha_n + \beta_n \quad (2a)$$

The ray distance p, measured at right angles to the respective parallel ray n, from the axis of rotation 14 (or from the z-axis) is given by:

$$p_n = R_F \sin \beta_n \quad (2b)$$

As will be clear with the aid of the central ray $RP_z$, which is illustrated with a bold line and runs through the axis of rotation 14 or the x-axis, is, in the case of this ray, the central ray of the projection in fan beam geometry recorded in fan geometry for the focal position $F_Z$ at the focus angle $\alpha_z$. Since it is true that β=0 for the central ray of a projection recorded using fan beam geometry, it becomes clear that the following holds for the case of central rays:

Depending on whether an azimuthal rebinning or a complete rebinning is carried out, the parallel projections are present in the form P(α,β,q)

or in the form

P(θ,p,q)

in which case

α represents the focus angle,
β represents the fan angle,
q represents the row index, corresponding to the z-angle of the detector system,
θ=α+β represents the parallel fan angle,
p=$R_F$sin(β) represents the parallel coordinate, corresponding to the ray distance from the axis of rotation (system axis), and
$R_F$ represents the radius of the focal path.

Although mutually parallel rays are selected or sorted from different projections, or readings, in an azimuthal rebinning, these need not necessarily be equidistant, that is to say have a constant spacing from one another.

In a complete rebinning, the spacing of the parallel rays are brought to the same distance by interpolation, such that a parallel beam arrangement corresponding to FIG. 3 is produced or formed.

The respective embodiment of the rebinning as a possible optional operating mode can be set by means of the keyboard 19.

The essence of at least one embodiment of the present invention is now to modify the weighted filter back projection (WFBP) method already frequently mentioned and which has become popular in computed tomography such that imaging is possible although in accordance with spiral data acquisition the examination object moves at a different (that is to say variable) speed compared with the x-ray source detector unit (gantry) in accordance with spiral data acquisition, that is to say the CT system has a variable pitch during spiral scanning.

Without restriction of generality, the WFBP method is illustrated in detail below with the aid of a "complete rebinning".

The spiral path is fixed by the trajectory of the focus of the x-ray source and can be described as follows in the spatial domain (x-y-z-coordinate system) by the point coordinates of the focal position moving forwards spirally:

$$x_f = R_F \cos\alpha \ y_f = R_F \sin\alpha \ z_f = f(\alpha) \qquad (3)$$

with an arbitrary function f that describes the location of the table as a function of the focus angle $\alpha$, $R_F$ representing the radius of the spiral path.

The geometric description of an x-ray emanating from the spirally moved focus along the half line l ($l \in [0; \infty[$ ) in fan beam geometry is as follows:

$$x_{ray}(l) = R_F \cos\alpha - l\cos(\alpha + \beta) \qquad (4)$$

$$y_{ray}(l) = R_F \sin\alpha - l\sin(\alpha + \beta)$$

$$z_{ray}(l) = f(\alpha) + ql\tan\frac{\varphi}{2}$$

$\varphi$ describing the maximum aperture angle in the z-direction and q, $q \in [-1; 1[$, representing a counting parameter for the detector rows. Transformation into parallel beam geometry (FIG. 3) is based on the following equations, which can be used to undertake an appropriate rebinning:

$$\theta = \alpha + \beta \ p = R_F \sin\beta \qquad (5)$$

A row-wise rebinning ($\alpha$, $\beta$, q) → ($\theta$, p, q) by substituting these equations (5) into the equations (4) leads to the following system of equations that describes a spirally rotating x-ray:

$$x_{ray}(l) = \left(\sqrt{R_F^2 - p^2} - l\right)\cos\theta + p\sin\theta \qquad (6)$$

$$y_{ray}(l) = \left(\sqrt{R_F^2 - p^2} - l\right)\sin\theta + p\cos\theta$$

$$z_{ray}(l) = f\left(\theta - \arcsin\left(\frac{p}{R_F}\right)\right) + ql\tan\frac{\varphi}{2}$$

After measurement of all x-rays that have penetrated the object to be examined and struck the detector, information relating to the desired distribution $\mu_{x,y,z}$ of the attenuation coefficient is present only in the form of projection values $P_{x,y,z}(\theta,p,q)$ that can be illustrated in a sinogram. A back projection has to be performed in order to obtain $\mu_{x,y,z}$ itself. However, there is firstly a need for filtering (this is represented in mathematics as a "convolution"), since a direct back projection of the projection values (attenuation profiles) leads to image blurring. The convolution of the attenuation profiles before the back projection (that in essence constitutes high pass filtering) cancels out this blurring again.

The convolution of the acquired data is usually performed in a p-direction (FIG. 3) or in a $\beta$-direction (FIG. 1), that is to say respectively in the direction of the spiral tangent T belonging to the focal position of the central ray of the respective parallel projection (see FIG. 3), specifically by using a convolution core K customary in computed tomography (for example Shepp-Logan convolution core, Ramachandran-Lakshminarayanan convolution core, etc.)

$$P_{conv}(\theta,p,q) = \int dp' P(\theta,p',q) K(p-p') \qquad (7)$$

The convolution evidently constitutes filtering along the spiral tangent. Following filtering, a weighted back projection into the spatial domain is performed. This filtered back projection is carried out as follows:

The following sum $$V_{x,y,z}(\hat{\theta}) = \frac{1}{H_{x,y,z}(\hat{\theta})} \sum_{k,q} W(\hat{q}) P_{conv}(\hat{\theta} + k\pi, \hat{p}, \hat{q}) \qquad (8)$$

is formed for each voxel $V_{x,y,z}$ at the location (x,y,z) and for each projection angle $\hat{\theta} \in [0;\pi[$, where $\hat{p}$ is the column coordinate of the voxel $V_{x,y,z}$ that has been struck by at least one ray at the angle $\hat{\theta}$ $$\hat{p} = x\sin\hat{\theta} - y\cos\hat{\theta} \qquad (9)$$

and $\hat{q}$ represents the row coordinate of the voxel $V_{x,y,z}$ that has been struck by at least one ray at the angle $\hat{\theta}$ $$\hat{q} = \frac{z - f\left(\hat{\theta} - \arcsin\left(\frac{\hat{p}}{R_F}\right)\right)}{\hat{l}\tan\frac{\varphi}{2}} \qquad (10)$$

The auxiliary variable $\hat{l}$ for calculating $\hat{q}$ can be written as $$\hat{l} = \sqrt{R_F^2 - \hat{p}^2} - x\cos\hat{\theta} - y\sin\hat{\theta} \qquad (11)$$

The summation in equation (8) evidently means summing all the rays (or their detector values) that strike the voxel $V_{x,y,z}$ at the angle $\hat{\theta}$. Thus, all k rays from the same direction are accumulated, that is to say a count is made as to how many components k modulo $\pi$ are participating, something which differs depending on pitch and geometry. k is therefore the number of the half revolutions of the focus that are included in the reconstruction.

As a consequence of the selected filtering direction and of the summation both over k and over q, cone beam artifacts are avoided, firstly, and, secondly all the rays running through a voxel $V_{(x,y,z)}$ are taken into account in the interest of a highly effective dose usage.

Figure 5:
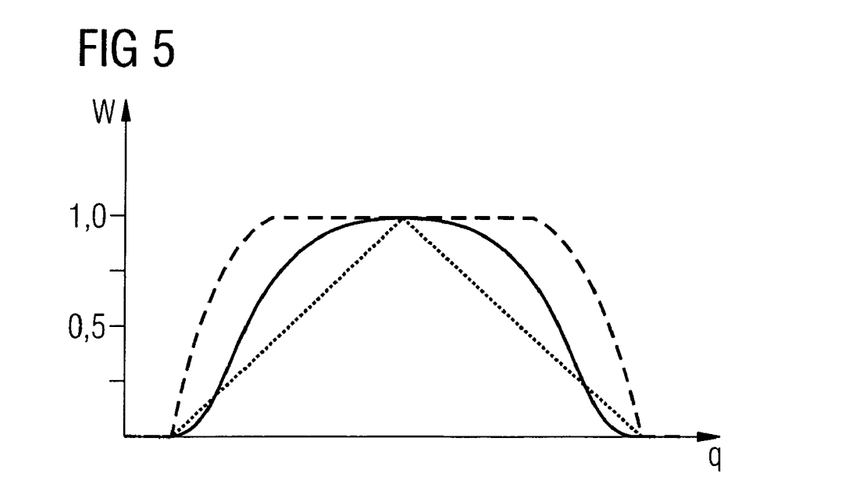
FIG. 5 shows a schematic of the diagrammatic profile of three different weighting functions W, and FIG. 6 a schematic of an offset ($\Delta z$) on the gantry in the z-direction, produced relative to the patient by spiral scanning.

Since the back projection algorithm is susceptible to artifacts owing to the sharp edges of the detector and/or to the rays near the margin, a valuation is undertaken in addition by W(q) depending on the position of a ray in the beam. W(q) represents a weighting function that weights near marginal rays positioned peripherally or at least decentrally in the beam with reference to its extent in the direction of the axis of rotation (extent in a column direction) than rays that are central. Thus, middle layers are given a high weighting, and outer layers a low one, which can be implemented by using different functions. Three examples of inventive profile of weightings W(q) are illustrated in FIG. 5. As is to be seen—common to all is a relatively strong weighting of the central rays compared to the outer rays. However, the functions are different. The dotted line represents a linearly falling profile to both sides of the center, while the dashed line produces an equal weighting over a large central region with a peripherally quickly falling tendency, and the continuous line exhibits a bell shaped profile that permits a soft transition between the extreme values 0 and 1.

$$= \sum_k W(q)$$

As is to be seen in equation (8), the back projection is normalized to the sum $$H_{x,y,z}\hat{\theta} = \sum_k W(q).$$

This enables a yet further improved image quality, since it removes a possible overemphasizing of voxels that are "illuminated" in a number (k) of half revolutions, that is to say struck by rays, and corresponding artifacts are thereby avoided. This redundancy occurs in the case of spiral scans whenever relative displacement per complete revolution of the measuring arrangement is so low (relatively low pitch) that voxels are multiply irradiated.

The absorption value, $\mu_{x,y,z}$ ultimately assigned to a voxel V(x, y, z) is obtained by summing over θ over at least one half revolution, that is to say by forming $$\mu_{x,y,z} = \sum_A P_{x,y,z}(\theta), \quad (12)$$

something which evidently corresponds to an accumulation of all the rays from the most varied angles θ at the location of voxel V(x, y, z). The CT number corresponding to the respective absorption value is determined in a conventional way from just this absorption value.

The mathematical form in which a variable pitch is taken into account by the invention is seen in equation (10), it being possible to use various approximations for $$f\left(\theta - \arcsin\left(\frac{\hat{p}}{R_F}\right)\right):$$

A) by taking account of the actual position of the parallel projection and the current pitch of the spiral, but linearizing the spiral profile locally:

$$f\left(\theta - \arcsin\left(\frac{\hat{p}}{R_F}\right)\right) \approx f(\theta) - \arcsin\frac{\hat{p}}{R_F} \cdot \frac{\partial f}{\partial \alpha}\bigg|_{a=\theta} \quad (11a)$$

B) by taking account of the actual position of the parallel projection and of the current pitch of the spiral, but approximating the spiral profile with the aid of an average pitch $$\frac{\partial f}{\partial \alpha}:$$

$$f\left(\theta - \arcsin\left(\frac{\hat{p}}{R_F}\right)\right) \approx f(\theta) - \arcsin\frac{\hat{p}}{R_F} \cdot \overline{\frac{\partial f}{\partial \alpha}} \quad (11b)$$

C) by approximating both the position of the parallel projection and the current pitch of the spiral with the aid of an average pitch $$\overline{\frac{\partial f}{\partial \alpha}}$$

and an effective start position $\alpha_{start}$ (for example from linear regression):

$$f\left(\theta - \arcsin\left(\frac{\hat{p}}{R_F}\right)\right) \approx \left((\theta - \alpha_{Start}) - \arcsin\frac{\hat{p}}{R_F}\right)\overline{\frac{\partial f}{\partial \alpha}} \quad (11c)$$

One of the three approximations (11a), (11b) or (11c) can be used depending on the degree of deviation of the function f from a linear profile.

Figure 4:
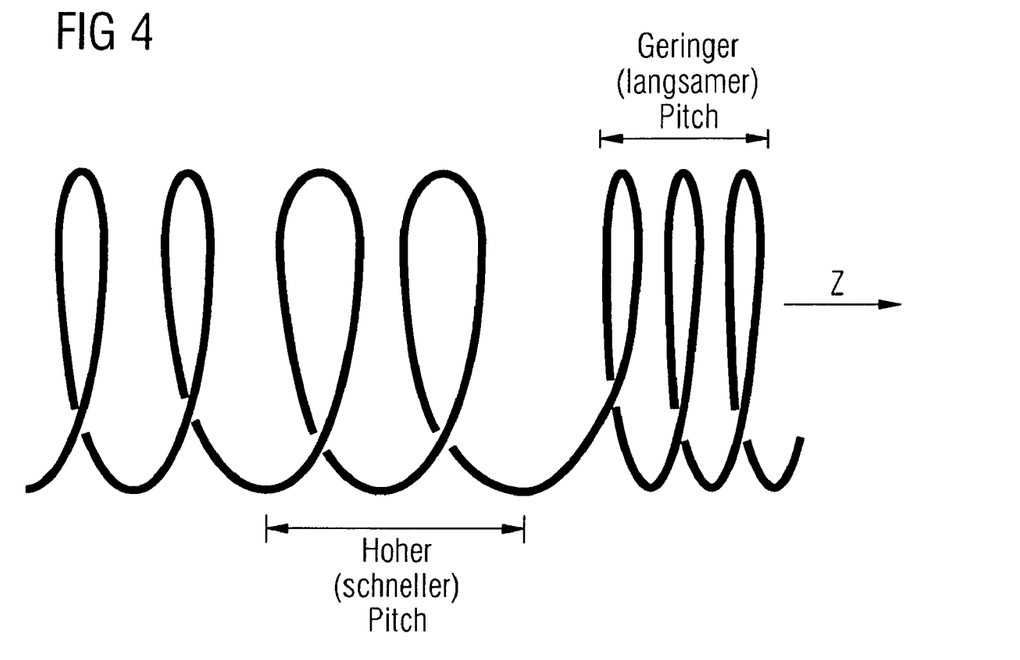
FIG. 4 shows a schematic of a multiply discontinuous spiral scanning in z-direction.

An inconsistent spiral owing to a variable z-feed or variable pitch (equation 1) is illustrated in FIG. 4. A high spiral path density results from a slow feed or small pitch value (equation 1), while a low spiral path density results from a fast feed or high pitch value (equation 1).

It is provided in the case of at least one embodiment of the inventive method to consider in conjunction with a voxel V(x,y,z) all the rays whose projection along the axis of rotation 14 or the z-axis passes through x, y. The weighting function W(q) determines whether and to what extent these rays are taken into account.

Figure 6:
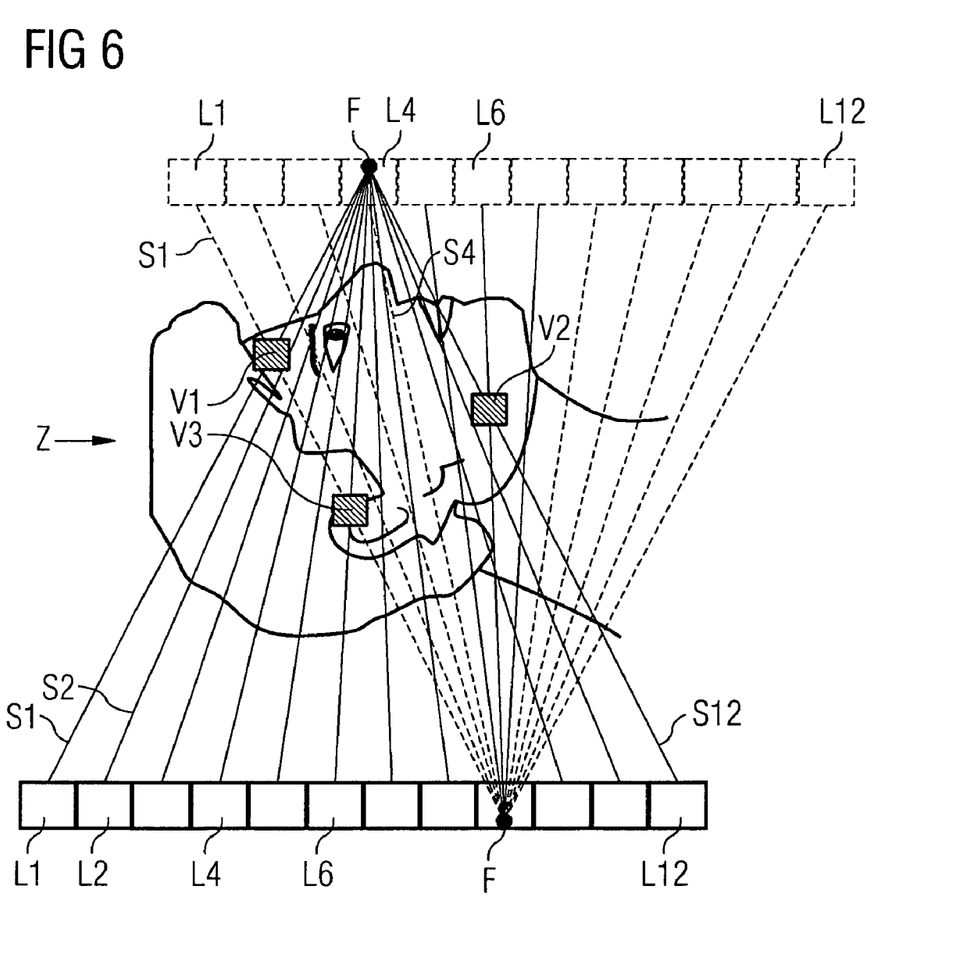

The mode of procedure of this weighting is demonstrated in a 2D representation in FIG. 6. In this example, the gantry of the CT with focus and detector in 0° position is drawn with full lines. The configuration (180° position) rotated by 180° about the z-axis is drawn with dashes. The detector has 12 detector rows L1 to L12 that are respectively struck by the assigned rays S1 to S12 of the beam. In may be remarked that the spatial dimensions shown with reference to the extent of the detector are represented with exaggeration in order to be able to explain the invention more clearly. The gantry shown moves in the most general case on an inconsistent spiral path around the z-axis or system axis in accordance with an arbitrary speed profile f (α) in a z-direction, although this cannot be illustrated in FIG. 6. However, FIG. 6 shows the beam of a gantry of a spiral CT in the 0° position and adjacent 180° position, respectively. In accordance with the nature of spiral CT, these positions are additionally offset from one another in the z-direction in addition to the rotation. In this illustration the voxel V1 is penetrated by the beam S1 both in the 0° position and in the 180° position. These two measurements are given a low evaluation in accordance with this decentral position of the beam S1 or of the associated detector row L1 lying outside in the detector. By contrast, the voxel V2 in the 0° position is penetrated by the decentrally lying beam S12 that is given a low weighting in this position for the voxel V2 but in the 180° position it is penetrated by the central beam S6 that is given a high weighting for this voxel V2. With reference to the voxel V1, these rays are both given a low evaluation in accordance with the position of the rays S1 in the 0° and 180° positions. Overall, this additional weighting W illustrated here results in substantial improvement in image quality.

In the case of the example embodiments described, the not necessarily constant relative movement between the measuring unit 1 and bearing apparatus 9 is respectively produced by virtue of the fact that the bearing apparatus 9, for example, is displaced at a different speed. However, it is also possible within the scope of the invention to leave the bearing apparatus 9 stationary and, instead, to displace the measuring unit 1 likewise at a different speed. Moreover, it is possible within the scope of at least one embodiment of the invention to produce a discontinuous relative movement by variable displacement both of the measuring unit 1 and of the bearing apparatus 9.

It may be remarked that in the case of the example embodiment described the conical x-ray beam has a rectangular cross section, but that other cross section geometries are also possible within the scope of the invention.

Third generation CT machines are used in conjunction with the above described example embodiments, that is to say the x-ray source and the detector system are displaced in common about the system axis during imaging. However, embodiments of the invention can also be used in conjunction with fourth generation CT machines in the case of which only the x-ray source is displaced about the system axis and cooperates with a fixed detector ring, insofar as the detector system is a multi-row array of detector elements.

Fifth generation CT machines, that is to say CT machines in the case of which the x-radiation emanates not only from one focus, but from a number of foci of one or more x-ray sources displaced about the system axis, can also use the inventive method insofar as the detector system has a multi-row array of detector elements.

The CT machines used in conjunction with the above described example embodiments have a detector system of the type of an orthogonal matrix of arranged detector elements. However, the invention can also be used in conjunction with CT machines whose detector system has in some other way an array with detector elements that is arranged on a surface.

The above described example embodiments relate to the medical application of the inventive method in CT. However, embodiments of the invention can also be applied outside medicine, for example in baggage checking or in material examination.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:
1. An imaging method for variable pitch spiral CT, comprising:
spirally scanning an examination object lying on a patient table, with the aid of a beam emanating from at least one focus, and with the aid of a 2 dimensional detector arrangement lying opposite the focus, the detector arrangement supplying record data;
rebinning the record data to output data, the output data being in parallel geometry and representing an attenuation of the beams during passage through the examination object;
filtering the output data;
weighted back-projecting the filtered output data; and
visualizing at least one of a layer and a volume on a display unit based upon the weighted back projected output data, a non constant pitch of the spiral scanning being taken into account computationally during the back projection, and the non constant pitch being described in the form of a function that describes a location of the patient table as a function of a focus angle, and function being expressed by a mathematical relationship between a projection angle, a column coordinate of the detector arrangement and a radius of the spiral, the mathematical relationship being approximated via one of the following,
a first approximation taking account of the actual position of a parallel projection and of the current pitch of the spiral and basing a local linearization of the spiral profile thereon,
a second approximation taking account of the actual position of a parallel projection and of the current pitch of the spiral and basing an approximation of the spiral profile in the form of an average pitch thereon, or
a third approximation being implemented by an approximation of the position of a parallel projection and of the current pitch of the spiral by way of an average pitch and an effective initial position of the focus angle.
2. The method as claimed in claim 1, wherein the function, in the case of the back projection, features in the calculation of the row coordinate.

3. The method as claimed in claim 2, wherein the focal path of spiral shape relative to the patient comes about by virtue of the fact that the focus is moved on a circular path about the system axis, and a relative movement between the focus and the examination object is performed simultaneously in the direction of the system axis.

4. A method as claimed in claim 2, wherein the detector arrangement includes detector elements arranged in matrix form in columns and rows.

5. A non-transitory computer readable medium including program segments for, when executed on a computer device, causing the computer device to implement the method of claim 2.

6. The method as claimed in claim 1, wherein the focal path of spiral shape relative to the patient comes about by virtue of the fact that the focus is moved on a circular path about the system axis, and a relative movement between the focus and the examination object is performed simultaneously in the direction of the system axis.

7. A method as claimed in claim 1, wherein the detector arrangement includes detector elements arranged in matrix form in columns and rows.

8. A method as claimed in claim 7, wherein the detector arrangement includes an orthogonal matrix of arranged detector elements.

9. A method as claimed in claim 7, wherein from a number of foci of one or more x-ray sources displaced about the system axis, can also use the inventive method insofar as the detector system has a multi-row array of detector elements.

10. A method as claimed in claim 1, wherein spirally scanning an examination object lying on a patient table is achieved with the aid of a beam emanating from a plurality of foci, and with the aid of a detector arrangement including a multi-row array of detector elements.

11. A method as claimed in claim 1, wherein spirally scanning an examination object lying on a patient table is achieved with the aid of a beam emanating from at least one focus, and with the aid of a detector arrangement including a multi-row array of detector elements.

12. A CT apparatus, comprising:
means for spirally scanning an examination object lying on a patient table, with the aid of a beam emanating from at least one focus, and with the aid of a detector arrangement of planar design lying opposite the focus, the detector arrangement supplying record data;
means for rebinning the record data to output data, the output data being in parallel geometry and representing an attenuation of the beams during passage through the examination object;
means for filtering the output data;
means for weighted back-projecting the filtered output data; and
means for visualizing at least one of a layer and a volume on a display unit based upon the weighted back projected output data, a non constant pitch of the spiral scanning being taken into account computationally during the back projection, and the non constant pitch being described in the form of a function that describes a location of the patient table as a function of a focus angle, and function being expressed by a mathematical relationship between a projection angle, a column coordinate of the detector arrangement and a radius of the spiral, the mathematical relationship being approximated via one of the following,
a first approximation taking account of the actual position of a parallel projection and of the current pitch of the spiral and basing a local linearization of the spiral profile thereon,
a second approximation taking account of the actual position of a parallel projection and of the current pitch of the spiral and basing an approximation of the spiral profile in the form of an average pitch thereon, or
a third approximation being implemented by an approximation of the position of a parallel projection and of the current pitch of the spiral by way of an average pitch and an effective initial position of the focus angle.

13. A non-transitory computer readable medium including program segments for, when executed on a computer device, causing the computer device to implement the method of claim 1.

* * * * *